(12) United States Patent
Companion

(10) Patent No.: US 8,221,337 B2
(45) Date of Patent: Jul. 17, 2012

(54) SYSTEM AND METHOD FOR MONITORING BLADDER DISTENTION IN A VARIETY OF PATIENTS HAVING DIFFERING ANATOMICAL PROPORTIONS

(75) Inventor: John A. Companion, Newport News, VA (US)

(73) Assignee: ODU Research Foundation, Norfolk, VA (US)

( * ) Notice: Subject to any disclaimer, the term of this patent is extended or adjusted under 35 U.S.C. 154(b) by 436 days.

(21) Appl. No.: 12/459,503

(22) Filed: Jul. 2, 2009

(65) Prior Publication Data

US 2011/0004123 A1 Jan. 6, 2011

(51) Int. Cl.
*A61B 5/103* (2006.01)
*A61B 8/00* (2006.01)
*G08B 23/00* (2006.01)
*G01S 3/80* (2006.01)

(52) U.S. Cl. ........ 600/587; 600/437; 600/438; 600/449; 600/459; 340/573.1; 340/573.5; 367/118; 367/129

(58) Field of Classification Search .................. 600/586, 600/587, 437, 438, 449, 459; 340/573.1, 340/573.5; 367/118, 119
See application file for complete search history.

(56) References Cited

U.S. PATENT DOCUMENTS

| | | | |
|---|---|---|---|
| 4,852,578 A * | 8/1989 | Companion et al. | 600/449 |
| 4,926,871 A | 5/1990 | Ganguly et al. | |
| 5,058,591 A | 10/1991 | Companion et al. | |
| 5,964,710 A | 10/1999 | Ganguly et al. | |
| 6,711,096 B1 * | 3/2004 | Benjamin | 367/162 |
| 2006/0100522 A1 * | 5/2006 | Yuan et al. | 600/466 |
| 2008/0294047 A1 * | 11/2008 | Kodama et al. | 600/449 |

OTHER PUBLICATIONS

Kristiansen, NK et al. "Design and evaluation of an ultrasound-based bladder volume monitor." Medical & Biological Engineering & Computing. 2004, v42, pp. 762-769.*

Kristiansen et al., "Design and evaluation of an ultrasound-based bladder volume monitor," Medical and Biological Engineering & Computing, 2004, pp. 762-769, vol. 42.

* cited by examiner

*Primary Examiner* — Max Hindenburg
*Assistant Examiner* — Megan Leedy
(74) *Attorney, Agent, or Firm* — Peter J. Van Bergen

(57) ABSTRACT

A system and method are provided for monitoring bladder distention. Independently controllable acoustic transmitters are coupled to the surface of a user's abdomen region in a spaced-apart fashion. Each transmitter can introduce a broadband acoustic signal into a portion of the abdomen region. Acoustic receivers are also coupled to the surface of the abdomen region to detect acoustic reflections generated when the acoustic signals are introduced into the abdomen region. A controller is positioned on the user and is correlated to an orientation of the user. The controller stores a profile indicative of anatomical features of the user. The controller initiates periodic activations of selected ones of the transmitters based upon the profile and the orientation of the user. The controller uses a weighted combination of all of the acoustic reflections to determine bladder distention of the user. The weighted combination is defined by at least the profile and orientation of the user.

24 Claims, 5 Drawing Sheets

SYSTEM AND METHOD FOR MONITORING BLADDER DISTENTION IN A VARIETY OF PATIENTS HAVING DIFFERING ANATOMICAL PROPORTIONS

FIELD OF THE INVENTION

The invention relates generally to bladder monitoring systems and methods, and more particularly to a system and method for monitoring bladder distention that can be adapted to function with a variety of patients having differing anatomical proportions.

BACKGROUND OF THE INVENTION

Urinary incontinence (UI) is a major health problem that affects as many as 25 million people in the United States at an estimated annual cost of nearly 20 billion dollars. Results of recent surveys of the United States population suggest that UI is a problem that is prevalent among 38% of adult women, over 50% of nursing home residents, and even up to 10-20% of children. Thus, UI affects a broad spectrum of the population where the members thereof will inevitably possess a broad range of anatomical proportions and anomalies, as well as have medical histories that can have an impact on a person's bladder filling and/or fluid retention capabilities.

Conventional approaches to dealing with UI have focused on the use of bladder monitors that include an acoustic system coupled to a patient's abdomen. These systems direct one or more acoustic beams into the abdomen and then sense the echoes generated when the acoustic beams reflect off the front and back walls of the patient's bladder. The echoes are processed in accordance with algorithms to determine bladder size or volume. Alarms are sounded, displayed, etc., when the bladder is full or nearly full. However, conventional systems tend to work well on specific members of the population (e.g., the young and/or thin patients) when those members are lying down or standing up. However, since UI is prevalent across a broad spectrum of ages, anatomical proportions, patients that are not always lying down or standing up, etc., conventional bladder monitors fall short of serving as an "every man" bladder monitor that can adapt to a particular patient's anatomical idiosyncrasies and/or body orientation.

SUMMARY OF THE INVENTION

Accordingly, it is an object of the present invention to provide a method and system of monitoring bladder distention.

Another object of the present invention is to provide a bladder distention monitoring method and system that can adapt to a wide variety of patient anatomies and/or body positions.

Other objects and advantages of the present invention will become more obvious hereinafter in the specification and drawings.

In accordance with the present invention, a system and method are provided for monitoring bladder distention. A plurality of independently controllable acoustic transmitters are coupled to the surface of a user's abdomen region in a spaced-apart fashion. A first portion of the transmitters is arranged on one side of the abdomen region relative to a vertical centerline thereof extending along the user's torso. A second portion of the transmitters is arranged on an opposing side of the abdomen region in an approximate mirror image fashion with respect to the first portion. A third portion of the transmitters is arranged on an upper region of the abdomen region. Each transmitter can introduce a broadband acoustic signal into a portion of the abdomen region. A plurality of acoustic receivers are also coupled to the surface of the abdomen region. Each receiver is positioned to detect acoustic reflections generated when the acoustic signals are introduced into the abdomen region. A controller is positioned on the user and is correlated to an orientation of the user. The controller stores a profile indicative of anatomical features of the user. The controller initiates periodic activations of selected ones of the transmitters from the first and second portions thereof based upon the profile and the orientation of the user. The controller also initiates selected activation of the third portion of the transmitters. The controller uses a weighted combination of all of the acoustic reflections to determine bladder distention of the user. The weighted combination is defined by at least the stored user profile and the orientation of the user. The controller generates an alarm signal when bladder distention indicates that a bladder voiding is needed.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
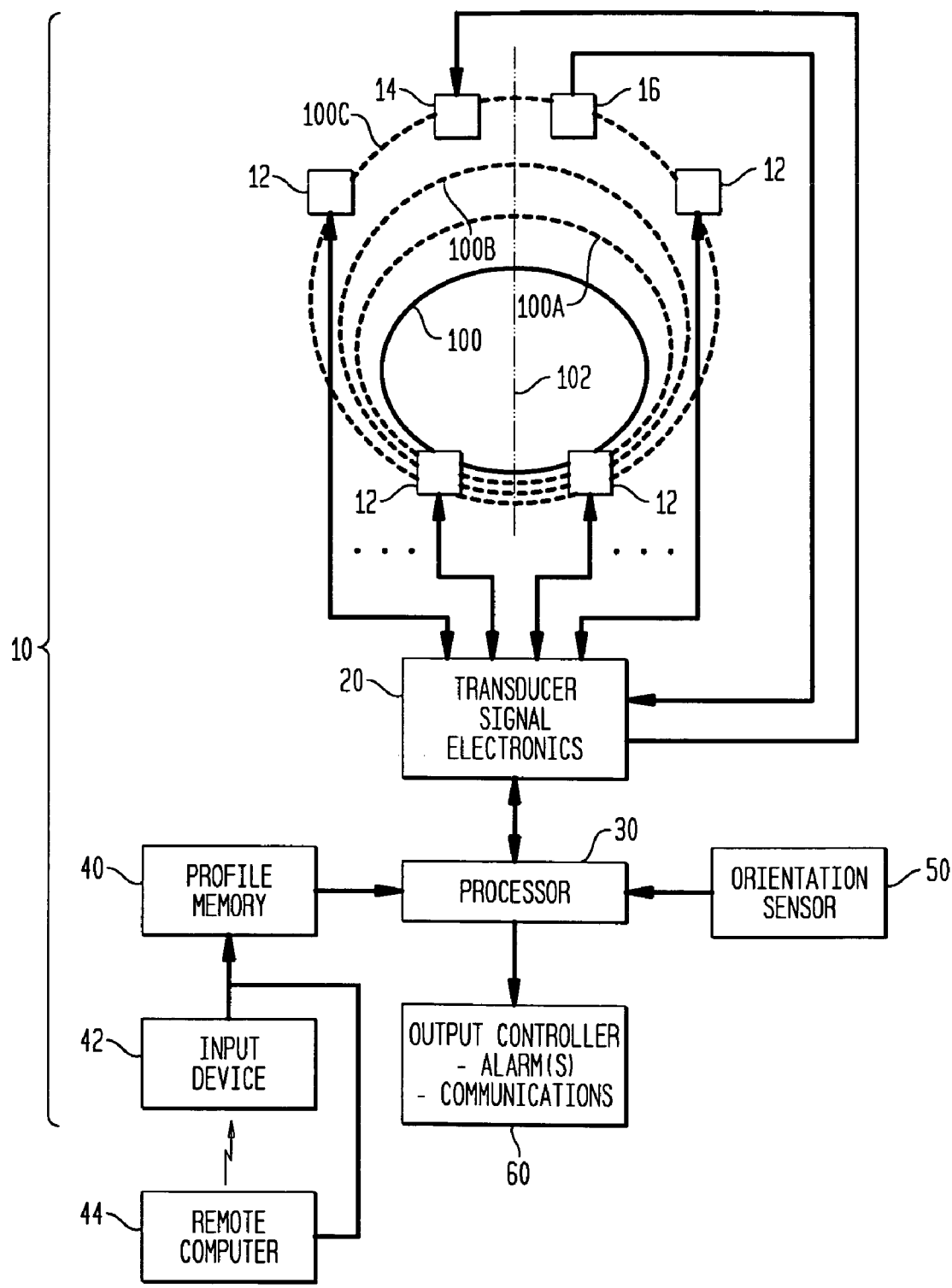
FIG. 1 is a schematic view of a bladder distention monitoring system in accordance with an embodiment of the present invention.

Referring now to the drawings and more particularly to FIG. 1, a bladder distention monitoring system in accordance with an embodiment of the present invention is shown and is referenced generally by numeral 10. System 10 is a non-invasive bladder monitor useful for the management of urinary incontinence (UI) problems. As will be explained herein, system 10 (as well as other embodiments of the present invention) address the issue of the wide physiological and anatomical variability in the target population suffering with UI. The present invention can be customized to the needs and situation of the individual patient.

To illustrate the scale of the problem to be addressed, urodynamic studies indicate that bladder size is highly variable between individuals, ranging from under 100 cubic centimeters to over 1500 cubic centimeters. There are also differences in the shape of the bladder, both in the non-distended and the distended state, and in the elevation relative to a patient's bony pelvis. It is also not uncommon for the bladder in a given individual to skew to the left or to the right during distension. Causes for this phenomenon include prior surgery, developmental idiosyncrasies, intestinal contents, non-uniform muscle tone, or a patient's body position or inclination, i.e. standing, sitting, lying down on one side or the other, etc. For elderly patients, bladder shape during distention can be significantly impacted by non-uniformity of muscle tone and body orientation. Other complicating factors include the possibility of organ prolapse due to, for example, pregnancy or a number of past pregnancies. The present invention is equipped for adaptation to the wide variety of anatomical and body position variability associated with the UI population.

In the illustrated embodiment, system 10 includes a number of composite acoustic transducers (i.e., a single device capable of both transmitting acoustic energy when activated and sensing/receiving acoustic energy when enabled). However, the present invention is not so limited as the system could use dedicated transmitters independently activated for sound transmission and dedicated receivers independently enabled for sound reception as will be explained later herein. The composite acoustic transducers (or separate acoustic transmitters and receivers) are placed in contact with a patient's skin in his/her abdomen region.

While the patient's skin/abdomen are not illustrated in FIG. 1, a patient's bladder is referenced by numeral 100 and possible relatively symmetric distention's of bladder 100 are referenced to dashed line outlines 100A, 100B and 100C. It is to be understood that the shape of bladder 100 and its distention's are presented solely to facilitate an understanding of system 10 since bladder distention can be symmetrical, but can also be anything but symmetrical. The present invention is designed to accommodate any asymmetry (or lack thereof) in the behavior of the bladder as it distends in any given individual. FIG. 1 presents a head-on view of bladder 100 with dashed line 102 representing a patient's approximate centerline. Distention's 100A-100C progressively push the top wall of bladder 100 towards the patient's head with distention 100C indicating a full or nearly full bladder condition.

The illustrated embodiment of the present invention uses at least four acoustic transducers 12 with typically half of the transducers being spaced apart from one another and placed on one side of centerline 102, and the other half being spaced apart from one another and placed on the other side of centerline 102. Each of transducers 12 is operated independently of any other transducer. That is, each of transducers 12 is independently controlled in terms of frequency and power. Directivity of each transducer is an inherent characteristic that is generally determined by the structure of the transducer. However, it is to be understood that the present invention could include active control of transducer directivity without departing from the scope of the present invention. Thus, operation of transducers 12 is governed by the construction of transducers 12, and the combination of transducer signal electronics 20 and a processor 30 as will be explained further below.

In general, transducers 12 are arranged to lie approximately along the sides of an inverted (with respect to a patient's head) trapezoid so that the two transducers 12 at the lowest part of the transducer arrangement are the closest to one another as shown. Each of transducers 12 is configured to introduce a broadband acoustic signal/wave into the patient's abdomen region. As will be explained further below, each transducer's acoustic signal/wave radiates in a generally conical fashion with some overlap typically occurring between signal/wave patterns from adjacent transducers so that the patient's abdominal region encompassing possible bladder distention is completely insonified regardless of which way the bladder distends.

To produce a broadband acoustic wave, each of transducers 12 is a type of piezoelectric transducer that produces an acoustic pulse comprised of a range of frequencies as an inherent characteristic of the physical construction of the transducer when an electrical drive signal is applied thereto. The class to which a given transducer belongs is defined by the fabrication technology used to build it. Conventional piezoelectric transducers are fabricated from a monolithic wafer of a ceramic material. Composite (broadband) piezoelectric transducers are fabricated from a large number of small ceramic fibers or posts, which are embedded in a polymeric matrix. Thin metallization layers are applied to the top and bottom faces and are processed to produce the piezoelectric effect. When an electrical drive signal is applied, the ceramic material "rings" just as a bell does when struck with a hammer. The frequency of the ring is controlled by a number of factors, but primarily by the thickness of the ceramic. Since a composite piezoelectric transducer's active material is not monolithic, it does not vibrate uniformly and therefore produces a range of frequencies when excited rather than a single peak. The lower edge of the produced frequency range is set by the thickness of the transducer while the range of produced frequencies is controlled by factors including fiber thickness, spacing between the fibers, and the distribution of the fibers in the polymeric matrix.

In the present invention, it is typical (but not essential) to use the same transducer to both produce an interrogating acoustic pulse (launched from the transducer into an adjacent volume of acoustically transmissive material such as human tissue) and to receive echoes of that interrogating pulse which are reflected back to the transducer from structures and interfaces within the interrogated volume. Regardless of whether standard or composite transducers are used, an acoustic wave front impinging on the face of a piezoelectric transducer sets up a vibration in the material that produces an electrical pulse characteristic of the impinging acoustic waveform.

Figure 2:
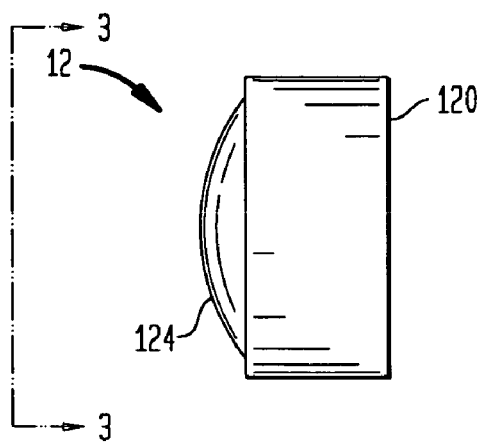
FIG. 2 is a side view of a composite acoustic transducer in accordance with an embodiment of the present invention.
Figure 3:
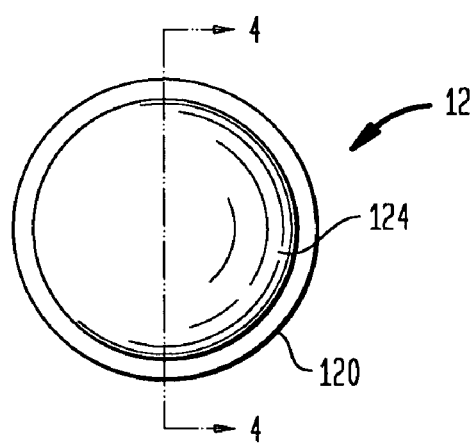
FIG. 3 is a top view of the transducer taken along line 3-3 in FIG. 2.
Figure 4:
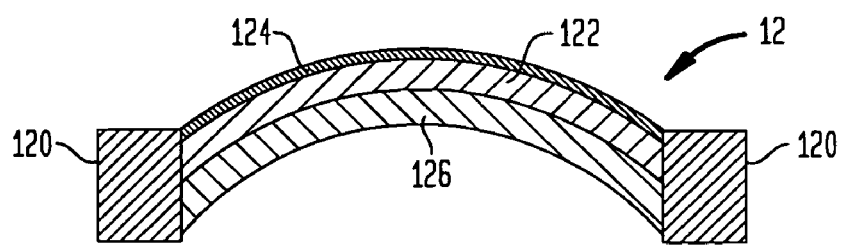
FIG. 4 is a cross-sectional view of the transducer taken along line 4-4 in FIG. 3.

While not a requirement of the present invention, each of transducers 12 can have its active element made from a piezo-composite material as described above. For example, each of transducers 12 could be configured as illustrated in FIGS. 2-4 where a holder 120 supports a semi-spherical or dome-shaped piezocomposite material layer 122 sandwiched between (i) one or more layers 124 of acoustic coupling material that provide for maximum sound transmission into/out of a patient's skin, and (ii) optional acoustic damping layer(s) 126 backing shaped piezocomposite 122.

Using shaped piezocomposite transducers provides novel functionality in the present invention. The piezocomposite transducers can be fabricated into a desired spherical segment configuration (e.g., size, amount of curvature, etc.) to customize the angle of divergence of the acoustic wave front produced by the transducer. Thus, each semi-spherical piezocomposite transducer 12 becomes the equivalent of a pulsating sphere. This is significant because by modulating the radius of curvature and frequency of these elements, the depth of acoustic wave penetration and the shape of the volume which each transducer insonifies can be readily controlled. This allows the present invention to address bladders that are low in the pelvic girdle and/or reside behind large amounts of fatty tissue typically found in obese patients. Further, by providing transducers 12 that are independently controllable, the present invention is uniquely able to adapt to a broad spectrum of anatomical proportions.

The present invention uses a broadband transmission for transducers 12 because in the application of ultrasonic interrogation of human tissue, resolution is directly related to frequency while depth of penetration of the ultrasound is inversely related to frequency. Higher frequencies will give improved resolution at shallow depths but will be absorbed as they pass through the tissue and any echoes will simply not get back to the transducer from greater depths. The present invention's use of broadband transmission schemes allows data to be harvested from both shallow and deep (relative to the transducers) volumes within the body and over a wide range of user variability as users can be slender children or obese adults. For example, a child will have a relatively small bladder that is close to the abdominal wall. Since the degree of distension of a small bladder occurs over a smaller range, it is desirable to have a higher resolution as compared to a large deep bladder for the same relative range of distension. On a small individual, some of the higher frequency components within the bandwidth of a piezocomposite transducer will penetrate to a sufficient depth to interrogate the volume containing the small bladder and be reflected back to the transducer(s). The lower frequency components penetrate more deeply, but can simply be excluded where they do not add useful data. Such exclusion can be accomplished by, for example, the use of time/range gating (i.e., time windowing of the acoustic wave front) in the signal processing. In this way, the highest-resolution returns can be used to view the abdomen region for a given patient. For a larger individual, the signal processing will use more of the lower frequencies as they will contain useful data in that case.

In general, the present invention uses a frequency spectrum for the broadband pulse that provides the maximum amount of data from the appropriate volumes within the abdomen for that individual. Typically, the lower end of the frequency range is approximately 500 KHz as this frequency will penetrate far enough into the abdomen to be able to interrogate the volumes of interest regardless of the body size of the user. The upper end of the frequency range is approximately 2 MHz as this frequency penetrates far enough into the abdomen to give sufficient resolution in the case of small individuals. Frequencies intermediate to this range will penetrate far enough to provide information about the effect of the bladder distension on the small intestines and the structures of the abdominal wall to harvest useful data showing the effects of the bladder distension on these areas. This data will be used in analysis schemes to help provide increased accuracy of tracking, especially in cases where the bladder itself is difficult to clearly track.

Transducer signal electronics 20 (e.g., conventional drivers, pre-amps, multiplexers, demultiplexers, signal conditioning, etc., as would be well understood in the art) and processor 30 cooperate to deliver the activation or enablement signals to each (or selected ones) of transducers 12 where each activated transducer introduces an acoustic signal/wave into the patient's abdomen. The activated transducers insonify an abdominal volume that can be thought of as a sub-dividable structure or a set of interrelated volumes, each containing a set of elements which can be different from that contained in other volumes. Because the interconnected volumes are composed of materials that will support the transfer of energy from elements in one volume to elements in the other interrelated volumes, energy producing or energy modulating activities in one volume can affect energy producing or modulating activities in adjacent volumes.

For the bladder distension monitoring function, the present invention performs qualitative data analysis of the energy content of various abdominal volumes to include:

the volume primarily containing the structures of the abdomen's anterior wall;
any intestinal structures that may be present between the abdominal wall and the front wall of the urinary bladder;
the abdominal volume primarily containing the urinary bladder;
the abdominal volume primarily containing the small intestine;
the abdominal volume containing the large blood vessels which pass posterior to the urinary bladder; and
in females who have not had a hysterectomy, the volume above and to the back of the urinary bladder that contains the uterus; although the analysis could be configured to ignore signals from this region for females that have had a hysterectomy.

Thus, each transducer's introduced signal/wave can encounter a variety of the anatomical structures depending on the location of the transducer on the patient, the patient's anatomical reality, and the patient's body position or orientation. The acoustic energy reflected by the encountered structures is detected by all of transducers 12 that are enabled for signal reception.

The present invention controls operation of transducers 12 based on a patient profile provided/stored in a memory 40 and the current body position/orientation of patient sensed by an orientation sensor 50. Sensor 50 can be coupled directly to the patient. Sensor 50 could also be maintained in a package or container that houses the other electronic components of system 10 where the package/container is then coupled to the patient or his clothing. Such orientation sensors (e.g., inclinometers) and their operation are well known in the art.

Memory 40 can be used to store look-up tables that define transducer activation/enablement schemes for a variety of general patient types and patient orientations. Each patient type can define a particular transducer activation/enablement scheme for each of a number of patient orientations where such orientations will affect responses of the transducers. A patient type designation for each such orientation could be referenced to readily-available patient information such as gender, age, weight, height, body mass index, pregnancy status, number of past pregnancies, past surgical procedures that can impact anatomical structures in the abdomen region, or any other category of information indicative of the patient's anatomical features. The various patient type designations and associated transducer activation/enablement schemes are generated through a comprehensive testing/evaluation of a test population. The number of such designations and schemes are not limitations of the present invention.

Once generated and stored in memory 40, a patient or caregiver performs a profile selection from one of the stored patient type designations that most closely resembles that of the actual patient. Such profile selection can be made by an input device 42 incorporated into system 10 or could be made via a remote computer 44 hardwired or wirelessly communicating with system 10. In cases where patient orientation is relevant, processor 30 uses the output of sensor 50 to select the transducer activation/enablement scheme associated with the selected patient type designation at that orientation.

At system start-up with transducers 12 coupled to a patient's abdomen, the particular transducer activation/enablement scheme is applied to transducers 12 and the returns or reflected acoustic energy from the patient's abdomen region are detected by enabled ones of transducers 12 and provided to processor 30. Note that a particular transducer activation/enablement scheme might not activate and/or enable all of transducers 12. For example, the lowermost ones of transducers 12 could be deactivated for a standing, elderly female patient with a large bladder capacity. This is because elderly women frequently have a fundamental weakness in the floor of the abdominal cavity causing the bladder to be low in the pelvis such that the bladder does not crest the pubis when the patient is standing. However, when this same type of patient sits, the repositioning of the legs will generally be sufficient to push the bladder higher and permit better observation using the lowest ones of transducers 12.

Processing of the returns detected by transducers 12 can proceed in accordance with a variety of data analysis schemes without departing from the scope of the present invention. Similar to the patient type designations stored in memory 40, suitable data analysis schemes can be developed and stored by processor 30. The number of such data analysis schemes can correspond directly with the number of patient type designations, or could be more or less without departing from the scope of the present invention. Further, the present invention can be configured to allow patient and/or caregiver fine tuning of a data analysis scheme's parameters for additional customization.

Each data analysis scheme is chosen to accentuate data harvested from volumes of the abdomen that provide the most useful tracking data for a particular patient type designation. In general, the signals representative of bladder distension have a time component and an energy component. The time component includes:

(i) the returning echo occurrence relative to the point in time when the interrogating pulse was launched into the abdomen (i.e., effectively a distance measurement as the speed of sound in the structures and tissues of the abdomen is a constant equal to approximately 1.5 millimeters per microsecond); and (ii) an assessment of the physical thickness of the area in which the activity is taking place. For example, when the bladder becomes relatively distended for adult males, the back wall moves into proximity to the two large veins that pass along the inner surface of the abdominal cavity into the muscles of the leg. The pulsations of these veins due to the heart beat is impressed upon the signal which represents the back wall of the bladder, causing the bladder to move physically back and forth in response. This position shift has the effect of causing an apparent increase in the thickness of the volume in which the bladder's back wall appears. Thus, a time modulation appears in the signal to serve as a further datum to assess bladder distension.

Figure 5A:
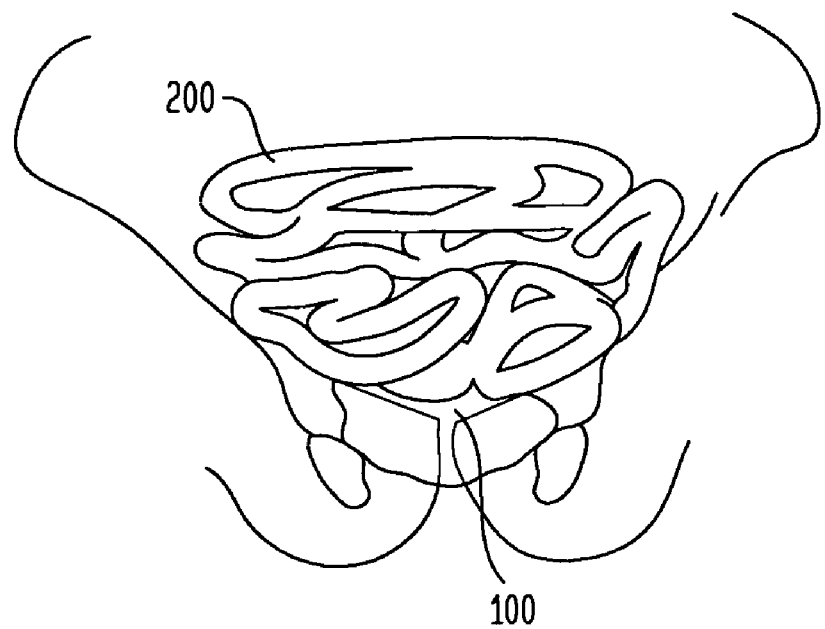
FIG. 5A illustrates the front view of a patient's pelvic region with isolated depiction of the patient's intestines and non-distended bladder.
Figure 5B:
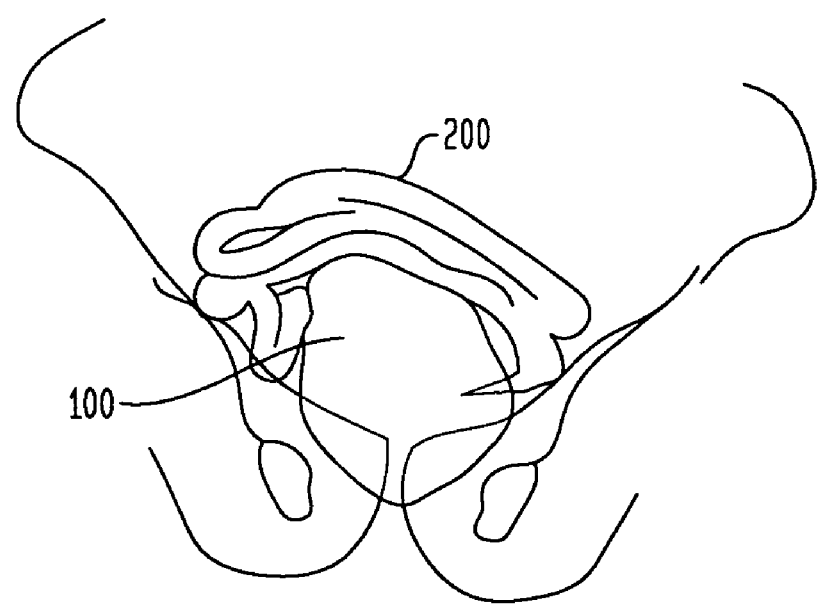
FIG. 5B illustrates the front view of a patient's pelvic region with the isolated depiction of the patient's intestines and distended bladder.

In addition to using transducers 12, the present invention includes a secondary sensing system for tracking bladder distention by tracking echogenic reflections from the patient's intestines. Tests of the present invention have led to the discovery that bladder distention compresses the small intestines which normally have a significant level of echogenicity when they are not compressed. That is, small intestine compression causes a reciprocal decline in echogenicity of the small intestines. This anatomical situation is depicted in FIGS. 5A and 5B where FIG. 5A illustrates intestines 200 relative to a non-distended bladder 100 and FIG. 5B illustrates intestines 200 relative to a distended bladder 100.

Based on this discovery, the present invention includes a separate acoustic transmitter 14 (e.g., a piezocomposite semi-spherical transmitter) and at least one separate acoustic receiver 16 (e.g., a PVDF acoustic sensor/receiver), both of which are positioned at the upper portion of the abdomen region or, typically, higher than any of transducers 12. The use of a separate (PVDF) receiver 16 will provide a higher degree of sensitivity to echoes from the intestines where such echoes can be lower in intensity as compared to echoes generated by the bladder. However, it is to be understood that single composite transducer may be sufficient if acceptable signal sensitivities are achieved. If more than one sensor/receiver is used, they can be positioned on either side of transmitter 14.

Transmitter 14 is configured and positioned to direct broadband acoustic energy toward the patient's intestines. In terms of transmitter 14, the term "broadband" encompasses a frequency range chosen to interact optimally with the lower amplitude and closer spaced echoes that will generally be produced by the peristaltic activities of the small intestines, as well as the changes in that activity that are caused by the compression applied to the intestines by the distension of the bladder from below.

Broadband transmission is used for transmitter 14 because there typically is variability in the physical structure of the intestines related to the body size of the individual and possibly to other conditions such as prior abdominal surgery. For most individuals, the above-identified frequency range for transducers 12 will also be a satisfactory frequency range of operation for transmitter 14. However, the particular frequency range used for transmitter 14 can be different than that used for transducers 12 without departing from the scope of the present invention. By tracking changes in responses detected by sensor/receiver 16, the present invention develops an independent and corroborating data set for monitoring bladder distention.

Processor 30 can use returns from transducers 12 and sensor/receiver 16 in a weighted fashion depending on the patient type designation and/or patient orientation. For example, a patient type designation having different "upright" and "sitting" transducer activation/enablement schemes might also weight the returns received at transducers 12 and sensor/receiver 16 differently for each such orientation. In this way, the present invention adjusts its sensitivity to the data that is most reliable for a given patient type and their current body position or orientation.

As described above, transducers 12 and transmitter 14 are activated in accordance with an activation scheme associated with a patient type designation and patient orientation. Regardless of the particular activation scheme, acoustic signals/waves are typically periodically introduced into the abdomen region. The particular period can be constant or can be varied between bladder voiding without departing from the scope of the present invention. In terms of a variable period for activation, the period between successive activations could be longer immediately after a bladder voiding with the period being decreased over time as a bladder presumably distends.

Processor 30 tracks the returns from transducers 12 and sensor/receiver 16 in order to monitor bladder distention. When the returns are indicative of a "filled" bladder that must be voided, processor 30 issues a signal to an output controller 60 where one or more alarms are generated and/or the signal is communicated/transmitted to one or more remote locations via a hardwire or wireless transmission scheme. The alarm(s) can be visual, audible, tactile, etc., for discernment by the patient and/or caregiver. Alarm choices can be selected and/or adjusted in accordance with patient and/or caregiver needs or preferences. In terms of signals transmitted by output controller 60, such signals can be machine/computer discernible and/or ultimately reproduced for discernment by a human.

It is to be understood that what constitutes a "filled" bladder will vary from patient-to-patient for a given set of circumstances. Accordingly, it is anticipated that a threshold (typically maintained by processor 30) indicative of a filled bladder for any patient can be made adjustable. Such adjustment can be made by any of a variety of ways without departing from the scope of the present invention.

Processor 30 can also include the capability to store time histories of the returns collected by transducers 12 and sensor/receiver 16. The time histories could be used to adjust the weights applied to the returns. In this way, the present invention can customize the weights associated with the originally-selected general patient type designation by re-specifying the weighted value of returns collected by transducers 12 and sensor/receiver 16.

Figure 6:
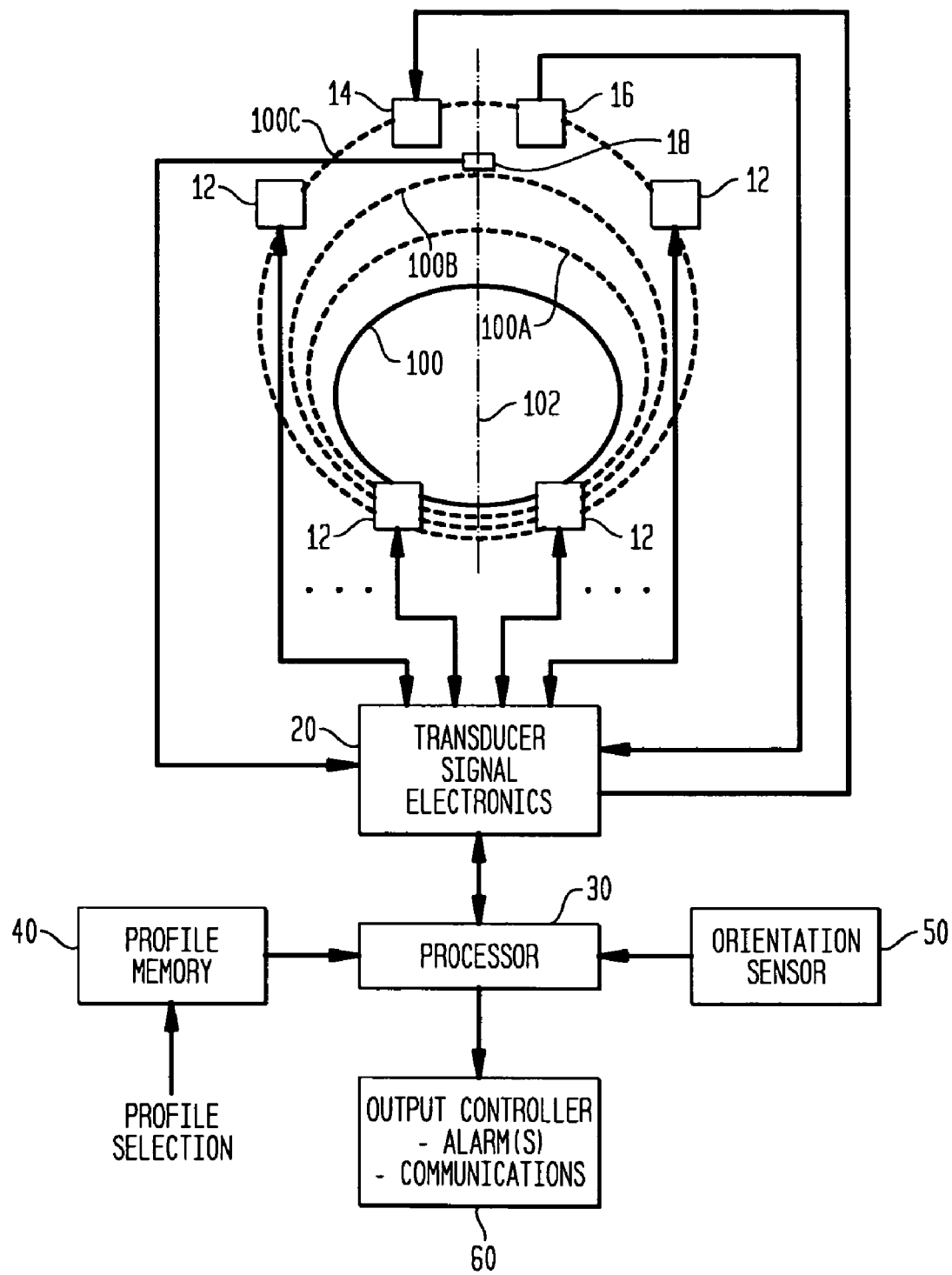
FIG. 6 is a schematic view of a bladder distention monitoring system in accordance with another embodiment of the present invention.

The present invention's ability to adapt to a patient's anatomical idiosyncrasies could be further enhanced with the use of a passive microphone for monitoring abdominal sounds which can change as a bladder fills. Accordingly, FIG. 6 illustrates another embodiment of the present invention where a passive microphone 18 (e.g., a digital microphone) is positioned on the patient's abdomen region at a location of choice. While the particular placement of microphone 18 can be varied for a particular patient, it will typically be located centrally on the upper portion of the patient's abdomen region. Processor 30 could also be programmed to record a time history of the sound that is detected by microphone 18. Since microphone 18 is passive, power requirements therefor are minimal so that the time history can be a continuous record. This time history could be used for later analysis or to adjust the weights applied to the returns of transducers 12 and sensor/receiver 16.

Figure 7:
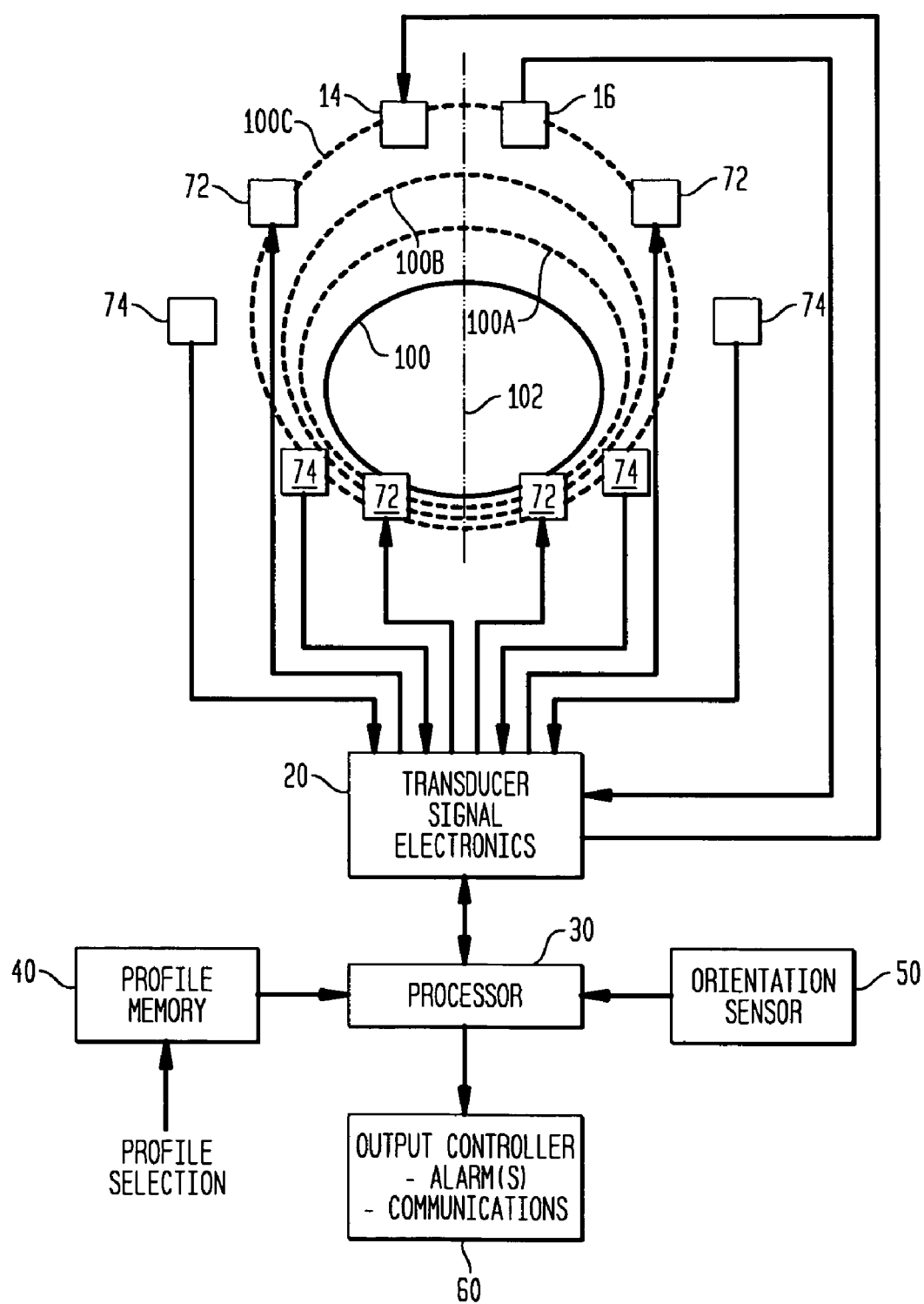
FIG. 7 is a schematic view of a bladder distention monitoring system in accordance with yet another embodiment of the present invention.

While the above-described embodiments of the present invention use composite transducers 12 to both introduce and receive acoustic energy, the present invention is not so limited. For example, the embodiment illustrated in FIG. 7 uses separate acoustic transmitters 72 and separate acoustic receivers 74 to perform the transmit and receive functions, respectively, of transducers 12. The number of transmitters 72 and receivers 74 can be the same or different without departing from the scope of the present invention.

Regardless of the embodiment used, the present invention operates in essentially the same fashion. Once the initial patient type designation is selected from memory 40, the abdomen region is interrogated and bladder distension signature characteristics can be recorded during an actual fill-to-void cycle at multiple points during the distension. An initial set of data is acquired during the course of a set of simple tests. One such set of tests includes:
  orienting the patient in accordance with a transducer activation scheme specified for a selected patient type designation and orientation;
  giving the patient a measured quantity of water immediately after a bladder voiding event; and
  interrogating the patient's abdomen in accordance with a predetermined schedule of interrogation.
Additional or alternative testing regimens can be used without departing from the scope of the present invention.

The advantages of the present invention are numerous. The bladder distension monitoring system and method acoustically interrogates a patient's lower abdomen on a periodic basis to track the relative distension of the bladder. A circumstance appropriate alarm can be indicated at a pre-selected distension level. The present invention uses multiple, individually-gathered data sets and then weights their value based on the patient's profile and body orientation to provide the most accurate tracking, even in difficult abdominal environments and/or orientations. The present invention is self-adapting to the typical behavior pattern of the bladder filling function of the individual patient. Because there are can be variations within the same individual, the present invention also provides the capability to track time histories of the various data sets, and adjust the weighted value of the data sets.

Although the invention has been described relative to a specific embodiment thereof, there are numerous variations and modifications that will be readily apparent to those skilled in the art in light of the above teachings. For example, with respect to the inclusion of a passive microphone, the system could include look-up tables that provide known acoustic data sets associated with various conditions (e.g., heart conditions, blood flow conditions, breathing conditions, etc.). The microphone data could then be compared to the known data sets and provide an alarm if/when one of the conditions is indicated by the recorded microphone data. The system's processor could also be programmed to use the data to determine, for example, bladder wall thickness as an indication of bladder cancer. It is therefore to be understood that, within the scope of the appended claims, the invention may be practiced other than as specifically described.

What is claimed as new and desired to be secured by Letters Patent of the United States is:

1. A system for monitoring bladder distention, comprising:
  a plurality, of independently controllable acoustic transmitters adapted to be coupled to the surface of a user's abdomen region in a spaced-apart fashion, wherein a first portion of said transmitters is arranged on one side of the abdomen region relative to a vertical centerline thereof extending along the user's torso, a second portion of said transmitters is arranged on an opposing side of the abdomen region in an approximate mirror image fashion with respect to said first portion, and a third portion of said transmitters is arranged on an upper region of the abdomen region, each of said transmitters including an active element made from a piezocomposite material for broadband acoustic transmission in a range from approximately 500 KHz to approximately 2 MHz, said piezocomposite material being semi-spherical in shape with a convex portion thereof being adapted to face the surface of the abdomen region when said transmitters are coupled thereto wherein each of said transmitters introduces a broadband acoustic signal into a portion of the abdomen region;
  a plurality of acoustic receivers adapted to be coupled to the surface of the abdomen region, each of said receivers positioned for detecting acoustic reflections generated when each said acoustic signal is introduced into the abdomen region; and
  a controller coupled to said transmitters and said receivers, said controller adapted to be positioned on the user and correlated to an orientation of the user, said controller storing a profile indicative of anatomical features of the user, said controller initiating periodic activations of selected ones of said transmitters from said first portion and said second portion based upon said profile and said orientation of the user wherein each said acoustic signal resulting from said periodic activations generates one of said acoustic reflections associated therewith for detection by one of said receivers,
  said controller initiating selected activation of said third portion of said transmitters wherein each said acoustic signal resulting from said selected activation generates one of said acoustic reflections associated therewith for detection by at least one of said receivers, and
  said controller using a weighted combination of all of said acoustic reflections to determine bladder distention of the user, wherein said weighted combination is defined by at least said profile and said orientation of the user, said controller generating an alarm signal when said bladder distention indicates that a bladder voiding is needed.

2. A system as in claim 1, wherein each of said transmitters from said first portion and said second portion is combined with one of said receivers to form a composite trancducer.

3. A system as in claim 1, wherein said controller includes a device for continually sensing orientation of said controller, and wherein orientation of said controller is indicative of said orientation of the user.

4. A system as in claim 1, wherein said first portion of said transmitters and said second portion of said transmitters so-arranged lie approximately along opposing sides of an inverted trapezoid shape.

5. A system as in claim 1, wherein said controller stores a time history of said acoustic reflections, and wherein said controller adjusts said weighted combination based on said time history.

6. A system as in claim 1, further comprising a microphone coupled to said controller and adapted to be coupled to the surface of the abdomen region wherein said controller records a time history of sound detected by said microphone, and wherein said controller adjusts said weighted combination based on said time history.

7. A system as in claim 1, further comprising at least one device coupled to said controller for converting said alarm signal to at least one of a human-discernable format and a machine discernable format.

8. A system as in claim 1, wherein frequency range is the same for each said acoustic signal introduced by said first portion of said transmitters and said second portion of said transmitters.

9. A system as in claim 8, wherein frequency range associated with each said acoustic signal introduced by said third portion of said transmitters is the same as that associated with first portion of said transmitters and said second portion of said transmitters.

10. A system as in claim 8, wherein frequency range associated with each said acoustic signal introduced by said third portion of said transmitters is different than that associated with first portion of said transmitters and said second portion of said transmitters.

11. A system for monitoring bladder distention, comprising:
a plurality of independently controllable acoustic composite transducers adapted to be coupled to the surface of a user's abdomen region in a spaced-apart fashion, wherein d first portion of said transducers is arranged on one side of the abdomen region and a second portion of said transducers is arranged on an opposing side of the abdomen region with said first portion and said second portion so-arranged lying approximately along opposing sides of a trapezoid shape that is inverted relative to the user's standing orientation, each of said transducers including an active element made from a piezocomposite material for broadband acoustic transmission in a range from approximately 500 KHz to approximately 2 MHz, said piezocomposite material being semi-spherical in shape with a convex portion thereof being adapted to face the surface of the abdomen legion when said transducers are coupled thereto wherein each of said transmitters introduces a broadband acoustic signal into a portion of the abdomen region and detecting acoustic reflections generated when each said acoustic signal is introduced into the abdomen region;

an acoustic transmitter/receiver arrangement adapted to be coupled the surface of an upper region of the abdomen region for transmitting broadband acoustic energy into the upper region towards the user's intestines and for detecting acoustic energy reflected by the intestines; and a controller adapted to be positioned on the user and coupled to said transducers and said transmitter/receiver arrangement, said controller continually detecting orientation of the user, said controller storing a profile indicative of anatomical features of the user, said controller initiating periodic activations of selected ones of said transducers based upon said profile and said orientation of the user wherein each said acoustic signal resulting from said periodic activations generates one of said acoustic reflections associated therewith for detection by one of said transducers, said controller initiating transmission of said acoustic energy into the upper region wherein said acoustic energy reflected from the intestines is detected, and said controller using all of said acoustic reflections and said acoustic energy reflected by the intestines in a weighted combination to determine bladder distention of the user wherein said weighted combination is defined by at least said profile and the orientation of the user, said controller generating an alarm signal when said bladder distention indicates that a bladder voiding is needed.

12. A system as in claim 11, wherein said controller stores a time history of said acoustic reflections, and wherein said controller adjusts said weighted combination based on said time history.

13. A system as in claim 11, further comprising a microphone coupled to said controller and adapted to be coupled to the surface of the abdomen region wherein said controller records a time history of sound detected by said microphone, and wherein said controller adjusts said weighted combination based on said time history.

14. A system as in claim 11, further comprising at least one device coupled to said controller for converting said alarm signal to at least one of a human-discernable format and a machine-discernable format.

15. A system as in claim 11, wherein frequency range is the same for each said acoustic signal introduced by said first portion of said transducers and said second portion of said transducers.

16. A system as in claim 15, wherein frequency range of said acoustic energy is the same as that associated with first portion of said transducers and said second portion of said transducers.

17. A system as in claim 15, wherein frequency range associated with said acoustic energy is different than that associated with first portion of said transducers and said second portion of said transducers.

18. A method of monitoring bladder distention, comprising the steps of:
positioning a plurality of independently controllable acoustic composite transducers on the surface of a user's abdomen region in a spaced-apart fashion, wherein a first portion of said transducers is arranged on one side of the abdomen region and a second portion of said transducers is arranged on an opposing side of the abdomen region with said first portion and said second portion so-arranged lying approximately along opposing sides of a trapezoid shape that is inverted relative to the user's standing orientation, each of said transducers including an active element made from a piezocomposite material for broadband acoustic transmission in a range from approximately 500 KHz to approximately 2 MHz, said piezocomposite material being semi spherical in shape with a convex portion thereof being defined, said step of positioning including the step of facing said convex portion of each of said transducers towards the surface of the abdomen region when said transmitters are coupled thereto;

positioning an acoustic transmitter/receiver arrangement on the surface of an upper region of the abdomen region;

activating selected ones of said transducers on a periodic basis based on a profile of the user indicative of anatomical features thereof and orientation of the user, wherein each of said transducers so-activated introduces a broadband acoustic signal into a portion of the abdomen region and detects acoustic reflections generated when each said acoustic signal is introduced into the abdomen region;

activating said transmitter/receiver arrangement for transmitting broadband acoustic energy into the upper region towards the user's intestines and for detecting acoustic energy reflected by the intestines;

processing a weighted combination of said acoustic reflections and said acoustic energy reflected by the intestines to determine bladder distention of the user wherein said weighted combination is defined by at least said profile of the user and said orientation of the user; and generating an alarm signal when said bladder distention indicates that a bladder voiding is needed.

19. A method according to claim 18, further comprising the steps of:
   storing a time history of said acoustic reflections; and
   adjusting said weighted combination based on said time history.

20. A method according to claim 18, further comprising the steps of:
   coupling a microphone to the surface of the abdomen region;
   recording a time history of sound detected by said microphone; and
   adjusting said weighted combination based on said time history.

21. A method according to claim 18, further comprising the step of converting said alarm signal to at least one of a human-discernable format and a machine-discernable format.

22. A method according to claim 18, wherein frequency range is the same for each said acoustic signal introduced by said first portion of said transducers and said second portion of said transducers.

23. A method according to claim 22, wherein frequency range of said acoustic energy is the same as that associated with first portion of said transducers and said second portion of said transducers.

24. A method according to claim 22, wherein frequency range associated with said acoustic energy is different than that associated with first portion of said transducers and said second portion of said transducers.

* * * * *